(12) United States Patent
Breyne

(10) Patent No.: US 6,203,729 B1
(45) Date of Patent: Mar. 20, 2001

(54) [PYRROLE]NAPHTHOPYRANES, THEIR PREPARATION, AND COMPOSITIONS AND (CO)POLYMER MATRICES CONTAINING THEM

(75) Inventor: Olivier Breyne, Lyons (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/444,477

(22) Filed: Nov. 19, 1999

(30) Foreign Application Priority Data

Nov. 20, 1998 (FR) .................................................. 98 14862

(51) Int. Cl.[7] ........................... G02B 5/23; C07D 487/00; C07D 207/00
(52) U.S. Cl. ...................... 252/586; 548/421; 548/407; 546/94; 546/276.7; 351/163
(58) Field of Search ............................. 252/586; 548/421, 548/407; 546/94, 276.7; 351/163; 523/135

(56) References Cited

U.S. PATENT DOCUMENTS

| | | | |
|---|---|---|---|
| 5,565,147 | * 10/1996 | Knowles et al. | 252/586 |
| 5,651,923 | 7/1997 | Kumar et al. | 252/586 |
| 5,674,432 | * 10/1997 | Knowles | 252/586 |
| 5,754,271 | 5/1998 | Guglielmetti et al. | 351/163 |
| 5,783,116 | * 7/1998 | Lin | 252/586 |
| 5,869,662 | * 2/1999 | Hughes | 252/586 |
| 5,891,368 | * 4/1999 | Kumar | 252/586 |
| 6,018,059 | * 1/2000 | Chan | 252/586 |
| 6,106,744 | * 8/2000 | Van Gemert | 252/586 |
| 6,113,812 | * 9/2000 | Hughes | 252/586 |

FOREIGN PATENT DOCUMENTS

| | | |
|---|---|---|
| 97/21698 | 6/1997 | (WO) . |
| 98/28289 | 7/1998 | (WO) . |
| 98/42693 | 10/1998 | (WO) . |
| 99/23071 | 5/1999 | (WO) . |

* cited by examiner

*Primary Examiner*—Philip Tucker
(74) *Attorney, Agent, or Firm*—Angela N. Nwaneri; Peter Rogalskyj

(57) ABSTRACT

Disclosed are naphthopyran-type compounds having a pyrrole group annelated in position 5.6, as well as compositions and particularly (co)polymer matrices containing them. These compounds, compositions, and matrices have photochromic properties. These [pyrrole]naphthopyran compounds have the general formula:

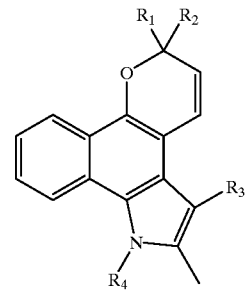

Articles containing these photochromic compounds, such as ophthalmic and/or solar glasses, lenses, glazing, devices, and the like, are also disclosed.

32 Claims, No Drawings

[PYRROLE]NAPHTHOPYRANES, THEIR PREPARATION, AND COMPOSITIONS AND (CO)POLYMER MATRICES CONTAINING THEM

The present invention relates to novel [pyirole] naphthopyran-type compounds which have, in particular, photochromic properties. The invention also relates to photochromic compositions and photochromic ophthalmic articles (lenses for example) which contain said [pyrrole] naphthopyrans. The invention also covers the preparation of these novel [pyirole]naphthopyrans. The photochromic compounds are capable of changing colour under the influence of a poly- or mono-chromatic light (UV for example) and of returning to their initial colour when the luminous irradiation ceases, or under the influence of temperature and/or a poly- or monochromatic light different from the first.

The photochromic compounds find applications in various fields, e.g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:

a high transmission in the absence of ultraviolets.

a low transmission (high colourability) under solar irradiation, adapted coloration and discoloration kinetics, a tint acceptable to the consumer (grey or brown preferably) with preferably a maintenance of the chosen tint during the coloration and the discoloration of the lens, a maintenance of the performances, the properties, within a temperature range of 0–40° C., a significant durability, since these objectives sought after are sophisticated corrective lenses and therefore expensive.

These lens characteristics are in fact determined by the active photochromic compounds which they contain ; compounds which must furthermore be perfectly compatible with the organic or inorganic support which constitutes the lens.

Moreover, it is to be noted that obtaining a grey or brown tint may necessitate the use of at least two photochromes of different colours, i.e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time and also for their compatibility with a plastic or inorganic support.

Amongst the numerous photochromic compounds described in the prior art, benzopyrans or naphthopyrans may be cited which are described in patents or patent applications U.S. Pat. No. 3,567,605, U.S. Pat. No. 3,627,690, U.S. Pat. No. 4,826,977, U.S. Pat. No. 5,200,116, U.S. Pat. No. 5,238,981, U.S. Pat. No. 5,411,679, U.S. Pat. No. 5,429,744, U.S. Pat. No. 5,451,344, U.S. Pat. No. 5,458,814, U.S. Pat. No. 5,651,923, U.S. Pat. No. 5,645,767, U.S. Pat. No. 5,698,141, WO-A-95 05382, FR-A-2,718,447, WO-A-96 14596, WO-A-97 21698 which are of the reduced formula below:

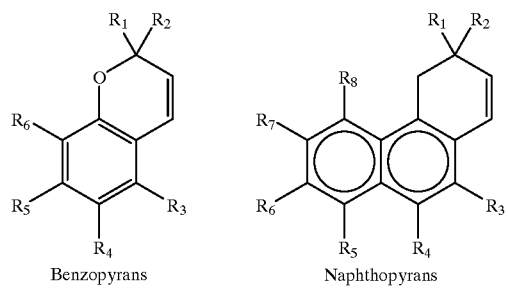

Benzopyrans    Naphthopyrans

The U.S. Pat. No. 5,651,923 notably claims the general structure below:

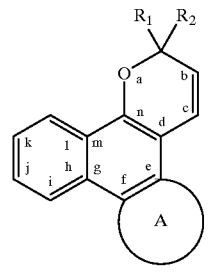

US-A-5,651,923 in which ring A, which is annelated with side $f$, is a benzothieno-, benzofurano- or indolo-type heterocycle.

These compounds claim to satisfy the specifications defined sulpra. In reality, if these compounds really do have one or more of the basic properties sought after, such as a high transmission in the absence of ultraviolets and a high colourability under solar irradiation, none of the compounds described hitherto have the complete combination of the properties sought after which are necessary for the production of satisfactory articles. In particular, none of these compounds is intrinsically grey or brown and the necessity of using an additional photochrome in order to obtain one of these two tints does subsist.

In this context, it is to the credit of the inventors for having been interested in this type of naphthopyran as a base for developing novel photochromes, and for having discovered a novel family of molecules which have particularly advantageous photochromic properties.

Thus, the present invention relates to [pyrrole] naphtlhopyran compounds of formula (I)

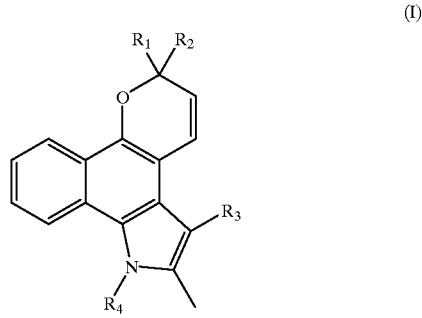

in which:

$R_1$ and $R_2$, which are identical or different, independently represent a hydrogen,
a linear or branched alkyl group which comprises 1 to 12 carbon atoms,
a cycloallkyl group which comprises 3 to 12 carbon atoms,
an aryl or heteroaryl group which comprises in its basic structure 6 to 24 carbon atoms or 4 to 24 carbon atoms respectively and at least one heteroatom selected from sulphur, oxygen and nitrogen; said basic structure being optionally substituted with at least one substituent selected from
  a halogen, and notably fluorine, chlorine and bromine,
  a hydroxy group,
  a linear or branched alkyl group comprising 1 to 12 carbon atoms,
  a linear or branched alkoxy group comprising 1 to 12 carbon atoms,
  a haloalkyl or haloalkoxy group corresponding to the ($C_1$–$C_{12}$) alkyl or alkoxy groups above respectively which are substituted with at least one halogen atom, and notably a fluoroalkyl group of this type,
  a linear or branched alkenyl group comprising 2 to 12 carbon atoms, and notably a vinyl group or an allyl group,
  an —$NH_2$ group,
  an -NHR group, R representing a linear or branched alkyl group comprising 1 to 6 carbon atoms,
  a

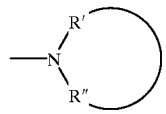

group, R' and R", which are identical or different, independently representing a linear or branched alkyl group comprising 1 to 6 carbon atoms, or representing together with the nitrogen atom to which they are bound a 5- or 7-membered ring which can comprise at least one other heteroatom selected from oxygen, sulphur and nitrogen, said nitrogen being optionally substituted with an R'" group, which is a linear or branched alkyl group comprising 1 to 6 carbon atoms,
  a methacryloyl group or an acryloyl group,
  an aralkyl or heteroaralkyl group, the alkyl part of which is linear or branched and comprises 1 to 4 carbon atoms, and the aryl part of which has the same definition as that given supra for the aryl and 1heteroaryl group;
or
  said two substituents $R_1$ and $R_2$ together form an adamantyl, norbornyl, fluorenylidene, di($C_1$–$C_6$) alkylantlhacenylidene or spiro($C_5$–$C_6$)cycloalkylanthracenylidene group; said group being optionally substituted with at least one of the substituents listed above for $R_1$, $R_2$: an aryl or heteroaryl group;
$R_3$ represents
  a methyl group,
  a $CR_5R_6OR_7$ group in which:
    $R_5$ and $R_6$, which are identical or different, represent independently, hydrogen or a linear or branched alkyl group, which comprises 1 to 6 carbon atoms,
    $R_7$ represents
      hydrogen,
      a linear or branched alkyl group which comprises 1 to 6 carbon atoms,
      an aralkyl group, the alkyl group comprising 1 to 3 carbon atoms and the aryl group is selected from a phenyl or naphthyl group optionally substituted with at least one of the substituents listed above for $R_1$, $R_2$ : an aryl or heteroaryl group,
      a $CH_2CN$ group,
      a $CH_2COOR_8$ group in which $R_8$ represents a hydrogen or a linear or branched alkyl group which comprises 1 to 6 carbon atoms,
      a $COR_9$ group in which $R_9$ represents a linear or branched alkyl group which comprises 1 to 6 carbon atoms, a cycloalkyl or bicycloalkyl group which comprises 3 to 12 carbon atoms, a phenyl or naphthyl group optionally substituted with at least one of the substituents listed above for $R_1$, $R_2$: an aryl or heteroaryl group,
      a —$COR_{10}$, —COORS, or $CONHR_{10}$ group, $R_{10}$ representing a linear or branched alkyl group comprising 1 to 6 carbon atoms, or a cycloalkyl group comprising 3 to 6 carbon atoms, or a linear or branched alkenyl group which comprises 2 to 12 carbon atoms, and notably an allyl group, or a phenlyl or benzyl group which is optionally substituted with at least one of the substituents listed above for the definition of $R_1$, $R_2$: an aryl or heteroaryl group;
R4 represents
  hydrogen,
  a linear or branched alkyl group which comprises 1 to 12 carbon atoms (advantageously 1 to 6 carbon atoms),
  a cycloalkyl group which comprises 3 to 12 carbon atoms,
  a linear or branched alkenyl group which comprises 2 to 12 carbon atoms, and notably a vinyl group or an allyl group,
  a phenyl or benzyl group, which is optionally substituted with at least one of the substituents listed above for the values of $R_1$, $R_2$: an aryl or heteroaryl group,
  a —$COR_{10}$, —$COOR_{10}$ or $CONHR_{10}$ group, $R_{10}$ representing a linear or branched alkyl group comprising 1 to 6 carbon atoms, or a cycloalkyl group comprising 3 to 6 carbon atoms, or a linear or branched alkenyl group which comprises 2 to 12 carbon atoms, and notably an allyl group, or a phenyl or benzyl group which is optionally substituted with at least one of the substituents listed above for the definition of $R_1$, $R_2$: an aryl or a heteroaryl group,
  a methacryloyl group or an acryloyl group.
Preferably, $R_1$ and/or $R_2$, which are identical or different, independently represent optionally substituted aryl or heteroaryl groups the basic structure of which is selected from those of phenyl, naphthyl, biphenyl, pyridyl, furyl, benzofuryl, dibenzofliryl, N—($C_1$–$C_6$)alkylcarbazole, thienyl, benzothienyl, dibenzothienyl, julolidinyl groups; $R_1$ and/or $R_2$ corresponding, more preferably still, to a phenyl group which is substituted in the para position, preferably substituted with an electron donor group and, more preferably still, with an amino or alkoxy group.
Preferably, $R_3$ represents
  a $CH_2OR_7$ group in which $R_7$ represents:
    hydrogen, a $COR_9$ group in which $R_9$ represents a linear or branched alkyl group which comprises 1 to 6 carbon atoms, a cycloalkyl or bicycloalkyl group which comprises 3 to 12 carbon atoms, an optionally substituted phenyl or naphthyl group, or a $COOR_{10}$ group, $R_{10}$ representing a linear or branched alkyl group comprising 1 to 6 carbon atoms or an optionally substituted phenyl or benzyl group.

Preferably, $R_4$ represents hydrogen or a linear or branched alkyl group which comprises 1 to 12 carbon atoms (advantageously 1 to 6 carbon atoms) or a phenyl or benzyl group, which is optionally substituted (with at least one of the substituents listed above for the definition of $R_1$, $R_2$: an aryl or a heteroaryl group).

The compounds of formula (I) in which $R_1$ and/or $R_2$, $R_3$, and $R_4$ have the above preferred values are particularly preferred.

The compounds of the invention—naphthopyrans of formula (I)—possess UV bands having a high λmax and a high colourability, even at 40° C. They have discolouration kinetics adapted to the applications sought after. The colours, which are easily accessible, vary from orange to violet.

As to the preferred means of preparing them, these compounds (I) can be obtained, generally, by the condensation:

of at least one compound of formula (II) below:

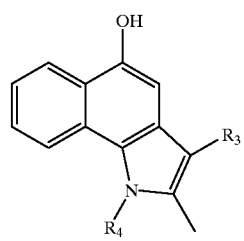

(II)

in which $R_3$ and $R_4$ are as defined with reference to formula (I) above, with a derivative of propargylic alcohol, of formula (III) below:

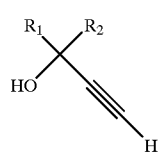

(III)

in which $R_1$ and $R_2$ are as defined with reference to formula (I) above (the condensation reaction may be carried out in solvents such as toluene, xylene or tetrahydrofuran in the presence of a catalyst such as para-toluenesulphonic acid or bromoacetic acid);

or with at least one aldehyde derivative, of formula (III') below:

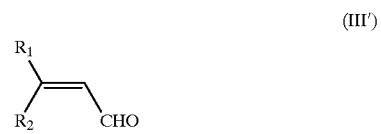

(III')

in which $R_1$ and $R_2$ are as defined with reference to formula (I) above (see for example EP-A-0 562 915), this condensation between (II) and (III') being carried out in the presence of a metallic complex—preferably a titanium complex (notably titanium (IV) ethoxide)—.

Thus, for this synthesis of the naphthopyrans of the invention, compounds of formula (II) on the one hand, and compounds of formula (III) or the corresponding aldehyde derivatives (III') on the other, are used.

Said compounds of formula (III) are known to the person skilled in the art and are obtained from the corresponding ketone according to a method described notably in the WO-A-96 14596 patent application. The ketone is itself commercial or is prepared according to the known methods such as the Friedel Crafts method (cf. WO-A-96 14596 and cited references). Aldehydes derived from (III), are obtained by rearrangement in an acid medium (cf. *J. Org. Chem.,* 1977, 42. 3403).

Said compounds of formula (II) are obtained by the condensation of 1,4-naphthoquinone with an aminocrotonate (cf. Patrick et al., *Tetrahedron Letters* 1979, p. 4009–12) of formula (IV):

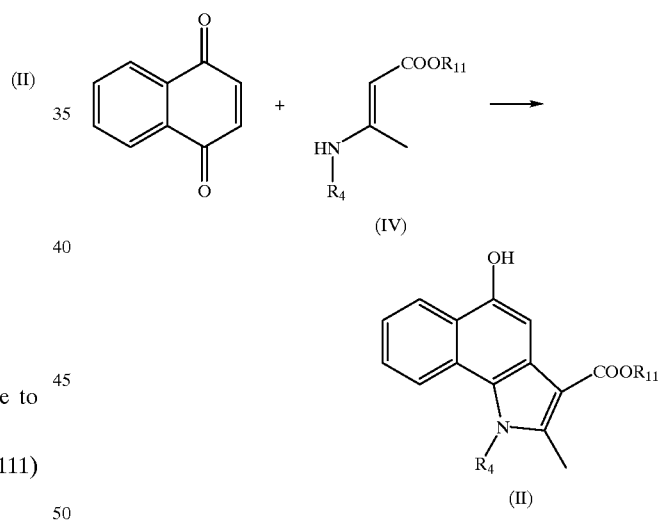

in which $R_{11}$ represents a linear or branched alkyl comprising 1 to 6 carbon atoms.

Classical modifications such as transesterification or reduction of the $COOR_{11}$ group enable various values of $R_3$ to be obtained.

Compounds (I) according to the invention have photochromic properties. From where it ensues that another object of the invention is photochromic products taken on their own or in mixtures of them, characterised in that they comprise compounds (I) as defined supra by their chemical structure or by the method of obtaining them.

These photochromic products based on compounds (I) of the [pyrrole]naphthopyran type can advantageously further comprise one or more other photochromic compounds which are different from compounds (I). Such combinations between [pyrrole]naphthopyrans (I) and photochromes of at least one other type are particularly interesting, given that it is possible for them to generate, for example, grey or brown tints, desired by the public in ophthalmic and/or solar applications, such as in the spectacles trade.

These additional photochromes can be those known to the person skilled in the art and described in the literature, for example chromenes (U.S. Pat. No. 3,567,605, U.S. Pat. No. 5,238,981, WO-A-94 22850, EP-A-0 562 915), spiropyrans or naphthospiropyrans (U.S. Pat. No. 5,238,981) and spiroxazines (CRANO et al., <<Applied Photochromiic Polymer Systems>>A, Ed. Blackie & Son Ltd. 1992, chapter 2).

According to another of its objects, the present invention relates to a composition, characterised in that it comprises -a- at least one of the photochromic products as defined supra;
-b- at least one receptor medium of the photochromic product(s)
-c- optionally at least one non-photochromic colouring agent;
-d- optionally at least one stabilising agent;
-e- optionally at least one anti-UV agent
-f- optionally at least one anti-radicals agent; and
-g- optionally at least one photochimic excited state deactivator.

iour in solution or in a polymer matrix, the compounds (I) according to the invention are colourless or slightly coloured in the initial state and rapidly develop an intense coloration under a UV light (365 nm) or under a light source of the solar type. Finally, they regain their initial coloration once the irradiation ceases.

The following products may be mentioned as examples of preferred polymer materials for optical applications of the photochromic compounds according to the invention:

alkyl, cycloalkyl, (poly or oligo)ethylene glycol, aryl or arylalkyl mono-, di-, tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, difunctional monomers having the formula below:

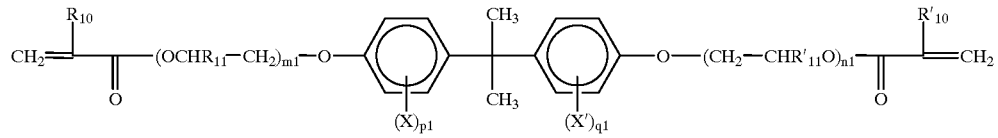

in which:

$R_{10}$, $R'_{10}$, $R_{11}$ and $R'_{11}$ are identical or different and represent independently a hydrogen or a methyl group;

ml and n, are, independently, integers between 0 and 4 (inclusive); and are advantageously independently equal to 1 or 2;

X and X', which are identical or different, are a halogen and represent, preferably, a chlorine and/or a bromine;

$p_1$ and $q_1$ are, independently, integers between 0 and 4 (inclusive);

copolymers of at least two types of copolymerisable monomers selected from the precursor monomers of the polymers listed supra, (notably selected from (meth)acrylic monomers, vinylic monomers, allylic monomers, and mixtures thereof).

In a particularly preferred manner, the photochromes of the invention are used with resins which have a nanobiphasic structure and which are obtained by copolymerising at least two different, specific difunctional monomers. Such resins have been described in the French patent application FR-A-2 762 845.

The methods of implementation which can be envisaged in order to obtain these cross-linked or non-cross-linked (co)polymer matrices are very varied. Amongst those known to the person skilled in the art, the diffusion in the (co) polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes According to a first means of implementation of the invention, the photochromic composition can be constituted by a solution in which at least one organic solvent plays the role of receptor medium -b-.

It therefore appears that the compounds of the invention can be used in solution, especially in the context of their photochromic applications. Thus, a photochromic solution can be obtained by dissolving at least one of said compounds in an organic solvent such as toluene, dichloromethane, tetrahydrofuran or ethanol. The solutions obtained are in general colourless and transparent. When exposed to sunlight, they develop a strong coloration and regain the colourless state when they are placed in an area of less exposure to the sun's rays or, in other words, when they are no longer submitted to UV. In general, a very low concentration of product (of the order of 0.01 to 5% by weight) is sufficient to obtain an intense coloration.

According to a second means of implementation of the invention, the photochromic composition can be constituted by a matrix-support in which at least one linear or branched and/or cross-linked (co)polymer and/or mineral material plays the role of receptor medium -b-.

In this second means of implementation, which is that which is prioritised, in accordance with the invention, the photochromic products of [pyrrole]naphthopyran type (I), even other different types (additional photochromes) can be included, even dispersed, within the matrix and/or applied to the surface of it as a coating. The most interesting applications of the compounds of the invention are in fact those in which the photochrome is dispersed uniformly within or on the surface of a matrix formed by a polymer, a copolymer and/or mixture of (co)polymers.

In and/or on these cross-linked or non-cross-linked (co) polymer matrices, and following the example of their behavto several hours, according to the nature of the polymer matrix. Another implementation technique consists in mixing the photochrome in a formulation of polymerisable matrices, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd—1992.

The amount of photochrome used in the (co)polymer matrix depends upon the degree of darkening desired. Usually, an amount of between 0.001 and 20% by weight of it is used.

According to a variant, compounds (I) according to the invention can be (co)monomers per se and/or be comprised in (co)monomers, which are (co)polymerisable and/or cross-linkable. The (co)polymers and/or reticulates thus obtained can constitute photochromic compositions or matrices. From where it ensues that the present invention also relates to a cross-linked or non-cross-linked (co)polymer, characterised in that it comprises, as (co)monomer(s), at least one of the photochromic products as defined supra.

The optional additives -c-, -d-, -e-, -f-, -g-, of the photochromic composition of the invention, are known to the person skilled in the art, who will know how to select them as a function of their use sought after.

The non-photochromic colouring agents -c- enable adjusting the tint.

The stabilising agents -d- such as anti-oxidising agents, anti-UV agents -e-, anti-radical agents -f-, and photochimic excited state deactivators -g-, can especially enable improving the durability of the photochromic composition.

According to another of its aspects, the present invention covers the use of the [pyrrole]naphthopyran compounds (I) as defined above by their chemical structure and by the method of obtaining them, as photocliromes, especially in the photochromic compositions as defined supra.

The invention finally relates to ophthalmic articles and/or solar articles comprising at least one of the ophthalmic products as defined supra
and/or at least one photochromic composition as defined supra
and/or at least one cross-linked or non-cross-linked (co)polymer as defined supra.

In practice the articles which are more particularly covered by the present invention are ophthalmic lenses or photochromic solar lenses, glazing (windows for buildings, for locomotion engines, automobile vehicles), optical devices, of which especially: decorative articles, solar protection articles, or information storage, . . . .

The present invention is illustrated by the Examples which follow of synthesis and of photochromic validation, of the [pyrrole]naphthopyrans of the invention (naphthopyrans). Said compounds of the invention are compared to a prior art compound, C1.

EXAMPLES

Example 1

Synthesis of Compound (1) ($R_1=R_2=$p—MeOC$_6$H$_4$; $R_3=$COOEt; $R_4=$Ph)

Step 1:

A solution of 12.8 g of 1,4-naphthoquinone and 16.5 g of ethyl anilinocrotonate in 50 ml of nitromethane is agitated 4 h at 40° C. and then one night at room temperature. The solid which precipitated is filtered, washed with nitromethane, and dried under vacuum. 15.05 g (56%) of a pink solid [compound of formula (II)] are obtained.

Step 2:

A few crystals of bromoacetic acid are added to a suspension of 1.53 g of 1,1-bis(para-methoxyphenyl)propyn-1-ol and 1.78 g of the compound from step 1 in 20 ml of xylene. Agitation is effected under reflux for I hi and the photochiome is then isolated by chromatography on a silica column (elution: pure toluene and then increasing concentrations of dichloromethane until pure dichloromethane). The red oil thus obtained is crystallised in a toluene/heptane mixture to give 2.14 g (70%) of a slightly pink powder. The structure is confirmed by $^1$H and $^{13}$C NMR.

Example 2

Synthesis of Compound (2) ($R_1=R_2=$p—MCOC$_6$H$_4$; $R_3=$COOMe; $R_4=$H)

Step 1:

A solution of 8 g of 1,4-naphthoquinone and 5.9 g of methyl 3-aminocrotonate in 50 ml of nitromethane is agitated one night at room temperature. The solid which precipitated is filtered, washed with diisopropyl ether, and dried under vacuum. 5 g (40%) of a dark powder [compound of formula (II)] are obtained.

Step 2:

A few crystals of bromoacetic acid are added to a suspension of 1.9 g of 1,1-bis(para-methoxyphenyl)propyn-1-ol and 1.5 g of the compound from step 1 in 50 ml of xylene. Agitation is effected under reflux for 1 h and the photochrome is then isolated by chromatography on a silica column (elution: heptane/ethyl acetate mixture 7/3). The red oil thus obtained is crystallised in a toluene/diisopropyl ether mixture to give 0.5 g (17%) of a pink powder. The structure is confirmed by $^1$H NMR.

Example 3

Synthesis of Compound (3) ($R_1=$C$_6$H$_5$; $R_2=$p—Me$_2$NC$_6$H$_4$; $R_3=$COOMe; $R_4=$H)

202 mg (21%) of a pink solid are obtained, according to a method identical to step 2 of Example 2, from 500 mg of the compound of step I of Example 2 and 590 mg of 1-(para-N-dimethylaminophenyl)-1-phenyl-propyn-1-ol in 30 ml of xylene.

Example 4

Synthesis of Compound (4) ($R_1=$p—MeOC$_6$H$_4$; $R_2=$p—Me$_2$NC$_6$H$_4$; $R_3=$COOMe; $R_4=$H)

160 mg (16%) of a pink solid are obtained according to a method identical to step 2 of Example 2 from 500 mg of the compound of step I of Example 2 and 660 mg of 1-(p-dimethylaminophenyl)-1-(p-methoxyphenyl)propyn-1-ol in 20 ml of xylene.

Example 5

Compound C1

Compound C1 of the prior art, of formula:

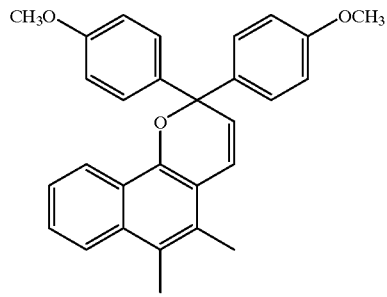

was considered.

This compound is commercially available.

The photochromic properties of said compounds (1) to (4) and C1 were evaluated. Said compounds are dissolved, at the rate of 5 mg in 50 ml of THF. The UV-visible absorptions (optical path of 1 cm) are then measured before and after exposure to a 365 nm UV source. The observation of the tints and intensities developed is made by placing the solutions in the sun or before a solar simulator. The properties of these compounds are given in the Table below.

| Compound | Structure | $\lambda_1$* | $\lambda_2$** | T½ (discoloration) | Tint/colourablility |
|---|---|---|---|---|---|
| (1) | [structure with COOEt, Ph, CH₃O and OCH₃ groups] | 378 nm | 516 nm | 40 s | red/high |
| (2) | [structure with COOMe, NH, CH₃O and OCH₃ groups] | 378 nm | 516 nm | 41 s | red/high |

-continued

| Compound | Structure | λ₁* | λ₂** | T½ (discoloration) | Tint/colourablility |
|---|---|---|---|---|---|
| (3) | [structure with NMe₂, phenyl, COOMe, pyrrole NH, methyl on naphthopyran] | 378 nm | 534 nm | 74 s | red/high |
| (4) | [structure with CH₃O, NMe₂, COOMe, pyrrole NH, methyl on naphthopyran] | 380 nm | 541 nm | 37 s | red/high |
| Cl | [structure with CH₃O, OCH₃, dimethyl naphthopyran] | 368 nm | 490 nm | 39 s | red/medium |

*λ max of the band of the longest wavelength of the compound before exposure.
**λ max of the band of the longest wavelength of the compound after exposure.

It is demonstrated by these measurements that the compounds of the invention have higher $\lambda_1$'s than the analogous compound without the ring annelated in position 5,6 of the naphthopyran, and this improves its sensitivity to solar radiation. The $\lambda_2$'s of the compounds are also higher (bathochromic shift) and the intensities developed in the presence of UV rays or solar rays are much higher than for the analogous compound.

What is claimed is:
1. A compound having the following formula (I):

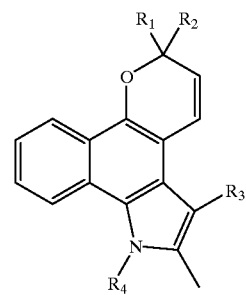

(I)

in which:

$R_1$ and $R_2$, which are identical or different, independently represent:
  a hydrogen,
  a linear or branched alkyl group which comprises 1 to 12 carbon atoms,
  a cycloalkyl group which comprises 3 to 12 carbon atoms,
  an aryl or heteroaryl group which comprises in its basic structure 6 to 24 carbon atoms or 4 to 24 carbon atoms respectively and at least one heteroatom selected from sulphur, oxygen, and nitrogen; said basic structure being optionally substituted with at least one substituent selected from:
    a halogen,
    a hydroxy group,
    a linear or branched alkyl group comprising 1 to 12 carbon atoms,
    a linear or branched alkoxy group comprising 1 to 12 carbon atoms,
    a haloalkyl or haloalkoxy group corresponding to the ($C_1$–$C_{12}$) alkyl or alkoxy groups above respectively which are substituted with at least one halogen atom,
    a linear or branched alkenyl group comprising 2 to 12 carbon atoms,
    an -NH$_2$ group,
    an -NHR group, R representing a linear or branched alkyl group comprising 1 to 6 carbon atoms,
    a

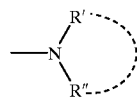

group in which R' and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, and
    a methacryloyl group or an acryloyl group, or
  an aralkyl or heteroaralkyl group, the alkyl part of which is linear or branched and comprises 1 to 4 carbon atoms, and the aryl part of which has the same definition as that given above for the aryl and heteroaryl group, or
  said two substituents, $R_1$ and $R_2$, together form an adamantyl, norbornyl, fluorenylidene, di($C_1$–$C_6$)alkylanthracenylidene, or spiro($C_5$–$C_6$)cycloalkylanthracenylidene group; said group being optionally substituted with at least one [of the substituents listed above for $R_1$, $R_2$ : an aryl or heteroaryl group] substituent selected from the group consisting of:
    a halogen,
    a hydroxy group,
    a linear or branched alkyl group comprising 1 to 12 carbon atoms,
    a linear or branched alkoxy group comprising 1 to 12 carbon atoms,
    a haloalkyl or haloalkoxy group corresponding to the ($C_1$–$Cl_2$) alkyl or alkoxy groups above respectively which are substituted with at least one halogen atom,
    a linear or branched alkenyl group comprising 2 to 12 carbon atoms,
    an —NH$_2$ group,
    an —NHR group, R representing a linear or branched alkyl group comprising 1 to 6 carbon atoms,
    a

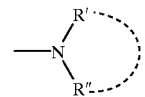

group in which R' and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, and
    a methacryloyl group or an acryloyl group;

$R_3$ represents:
  a methyl group,
  a $CR_5R_6OR_7$ group in which:
    $R_5$ and $R_6$ are identical or different and represent, independently, hydrogen or a linear or branched alkyl group which comprises 1 to 6 carbon atoms, and
    $R_7$ represents:
      hydrogen,
      a linear or branched alkyl group which comprises 1 to 6 carbon atoms,
      an aralkyl group, wherein the alkyl group comprises 1 to 3 carbon atoms and the aryl group is selected from a phenyl or naphthyl group optionally substituted with at least one substituent selected from the group consisting of:
        a halogen,
        a hydroxy group,
        a linear or branched alkyl group comprising 1 to 12 carbon atoms,
        a linear or branched alkoxy group comprising 1 to 12 carbon atoms,
        a haloalkyl or haloalkoxy group corresponding to the ($C_1$–$C_{12}$) alkyl or alkoxy groups above respectively which are substituted with at least one halogen atom,
        a linear or branched alkenyl group comprising 2 to 12 carbon atoms,
        an —NH$_2$ group,
        an —NHR group, R representing a linear or branched alkyl group comprising 1 to 6 carbon atoms,
        a

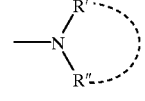

group in which R' and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, and
a methacryloyl group or an acryloyl group,
a $CH_2CN$ group,
a $CH_2COOR_8$ group in which $R_8$ represents a hydrogen or a linear or branched alkyl group which comprises 1 to 6 carbon atoms, or
a $COR$, group in which Rg represents a linear or branched alkyl group which comprises 1 to 6 carbon atoms, a cycloalkyl or bicycloalkyl group which comprises 3 to 12 carbon atoms, a phenyl or naphthyl group optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom,
a linear or branched alkenyl group comprising 2 to 12 carbon atoms,
an —$NH_2$ group,
an —NHR group, R representing a linear or branched alkyl group comprising 1 to 6 carbon atoms,
a

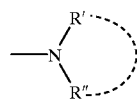

group in which R' and R'' are identical or different and independently represent a linear or branched alkyl group comprising 1 to 6 carbon atoms, or R' and R'', together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, and
a methacryloyl group or an acryloyl group, or
a —$COR_{10}$, —$COOR_{10}$, or $CONHR_{10}$ group, wherein $R_{10}$ represents a linear or branched alkyl group comprising 1 to 6 carbon atoms, or a cycloalkyl group comprising 3 to 6 carbon atoms, or a linear or branched alkenyl group which comprises 2 to 12 carbon atoms, or a phenyl or benzyl group which is optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom,
a linear or branched alkenyl group comprising 2 to 12 carbon atoms,
an —$NH_2$ group,
an —NHR group, R representing a linear or branched alkyl group comprising 1 to 6 carbon atoms,
a

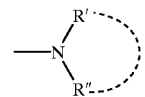

group in which R' and R'' are identical or different and independently represent a linear or branched alkyl group comprising 1 to 6 carbon atoms, or R' and R'', together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, and
a methacryloyl group or an acryloyl group; and
$R_4$ represents:
hydrogen,
a linear or branched alkyl group which comprises 1 to 12 carbon,
a cycloalkyl group which comprises 3 to 12 carbon atoms,
a linear or branched alkenyl group which comprises 2 to 12 carbon atoms,
a phenyl or benzyl group which is optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom,
a linear or branched alkenyl group comprising 2 to 12 carbon atoms,
an —$NH_2$ group,
an —NHR group, R representing a linear or branched alkyl group comprising 1 to 6 carbon atoms,
a

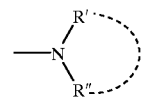

group in which R' and R'' are identical or different and independently represent a linear or branched alkyl group comprising 1 to 6 carbon atoms, or R' and R'', together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, and a methacryloyl group or an acryloyl group,
a —COR$_{10}$, —COOR$_{10}$, or CONHR$_{10}$ group, wherein R$_{10}$ represents a linear or branched alkyl group comprising 1 to 6 carbon atoms, or a cycloalkyl group comprising 3 to 6 carbon atoms, or a linear or branched alkenyl group which comprises 2 to 12 carbon atoms, or a phenyl or benzyl group which is optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the (C$_1$–C$_{12}$) alkyl or alkoxy groups above respectively which are substituted with at least one halogen atom,
a linear or branched alkenyl group comprising 2 to 12 carbon atoms,
an —NH$_2$ group,
an —NHR group, R representing a linear or branched alkyl group comprising 1 to 6 carbon atoms,
a

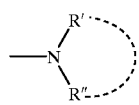

group in which R' and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R'" group which is a linear or branched alkyl group comprising 1 to 6 carbon atoms, and
a methacryloyl group or an acryloyl group, or
a methacryloyl group or an acryloyl group.

2. A compound according to claim 1, wherein:
at least one of R$_1$ and R$_2$ represent optionally substituted aryl or heteroaryl groups the basic structure of which is selected from those of phenyl, naphthyl, biphenyl, pyridyl, furyl, benzofuryl, dibenzoftiryl, N-(C$_1$–C$_6$) alkylcarbazole, thienyl, benzothienyl, dibenzothienyl, and julolidinyl groups;
R$_3$ represents:
a CH$_2$OR$_7$ group in which R$_7$ represents:
hydrogen,
a COR$_9$ group in which R$_9$ represents a linear or branched alkyl group which comprises 1 to 6 carbon atoms, a cycloalkyl or bicycloalkyl group which comprises 3 to 12 carbon atoms, or an optionally substituted phenyl or naphthyl group, or
a COOR$_{10}$ group in which R$_{10}$ represents a linear or branched alkyl group comprising 1 to 6 carbon atoms or an optionally substituted phenyl or benzyl group; and
R$_4$ represents hydrogen or a linear or branched alkyl group which comprises 1 to 12 carbon atoms or an optionally substituted phenyl or benzyl group.

3. A compound according to claim 2, wherein at least one of R$_1$ and R$_2$ corresponds to a para-substituted phenyl group.

4. A method of preparing a compound according to claim 1, wherein said method comprises:
condensing at least one compound of formula (II) below:

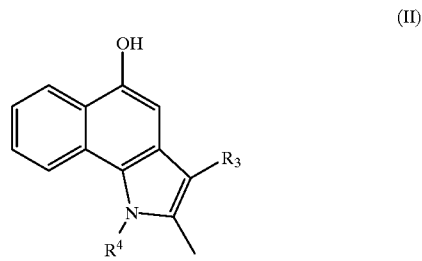

(II)

in which R$_3$ and R$_4$ are as defined with reference to formula (I) in claim 1
with a derivative of propargylic alcohol of formula (III) below:

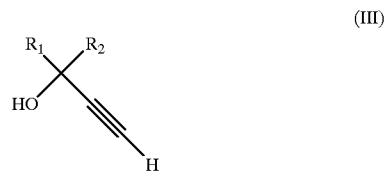

(III)

in which R$_1$ and R$_2$ arc as defined with reference to formula (I) in claim 1, wherein said condensing between (II) and (III) is optionally carried out in a solvent and in the presence of a catalyst,
or with at least one aldehyde derivative, of formula (III') below:

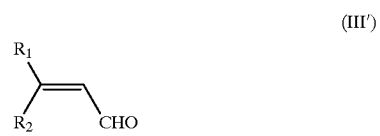

(III')

in which R$_1$ and R$_2$ are as defined with reference to formula (I) in claim 1, wherein said condensing between (II) and (III') is optionally carried out in the presence of a metallic tetraalkoxide.

5. A photochromic product comprising a compound according to claim 1.

6. A photochromic product according to claim 5, further comprising one or more other photochromic compounds which are different from those of formula (I).

7. A photochromic product comprising a compound prepared by a method according to claim 4.

8. A photochromic product according to claim 7, further comprising one or more other photochromic compounds which are different from those of formula (I).

9. A photochromic composition characterised in that it comprises:
-a- at least one photochromic product according to claim 5;
-b- at least one receptor medium of the photochromic product(s);
-c- optionally at least one non-photochromic colouring agent;
-d- optionally at least one stabilising agent;

-e- optionally at least one anti-UV agent;
-f- optionally at least one anti-radical agent;
-g- optionally at least one photochimic excited state deactivator.

10. A photochromic composition according to claim 9, wherein the at least one receptor medium comprises at least one organic solvent.

11. A photochromic composition according to claim 9, wherein the at least one receptor medium comprises a matrix-support comprising at least one linear or branched and/or cross-linked (co)polymer and/or at least one mineral.

12. A photochromic composition according to claim 9, wherein the at least one receptor medium comprises a matrix-support comprising at least one cross-linked or non-cross-linked (co)polymer selected the group consisting of:

alkyl, cycloalkyl, (poly or oligo)ethylene glycol, aryl or arylalkyl mono-, di-, tri-, or tetraacrylate, or mono-, di-, tri-, or tetramethacrylate which is optionally halogenated or which comprises at least one ether and/or ester and/or carbonate and/or carbamate and/or thiocarbamate and/or urea and/or amide group, polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, difunctional monomers having the formula:

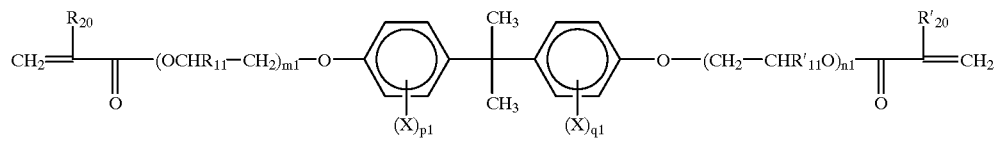

in which:
$R_{20}$, $R'_{20}$, $R_{11}$, and $R'_{11}$ are identical or different and represent, independently, a hydrogen or a methyl group;
$m_1$ and $n_1$ are, independently, integers between 0 and 4, inclusive;
X and X', which are identical or different, represent a halogen; and
$p_1$ and $q_1$ are, independently, integers between 0 and 4, inclusive, and copolymers of at least two types of copolymerisable monomers selected from the precursor monomers of the polymers listed above.

13. A cross-linked or non-cross-linked (co)polymer, characterised in that it comprises, as (co)monomer(s), at least one of the photochromic products according to claim 5.

14. A photochromic composition characterised in that it comprises:
-a- at least one photochromic product according to claim 7;
-b- at least one receptor medium of the photochromic product(s);
-c- optionally at least one non-photochromic colouring agent;
-d- optionally at least one stabilising agent;
-e- optionally at least one anti-UV agent;
-f- optionally at least one anti-radical agent;
-g- optionally at least one photochimic excited state deactivator.

15. A photochromic composition according to claim 14, wherein the at least one receptor medium comprises a solution comprising at least one organic solvent.

16. A photochromic composition according to claim 14, wherein the at least one receptor medium comprises a matrix-support comprising at least one linear or branched and/or cross-linked (co)polymer and/or at least one mineral.

17. A photochromic composition according to claim 14, wherein the at least one receptor medium comprises a matrix-support comprising at least one cross-linked or non-cross-linked (co)polymer selected the group consisting of:

alkyl, cycloalkyl, (poly or oligo)ethylene glycol, aryl or arylalkyl mono-, di-, tri-, or tetraacrylate, or mono-, di-, tri-, or tetramethacrylate which is optionally halogenated or which comprises at least one ether and/or ester and/or carbonate and/or carbamate and/or thiocarbamate and/or urea and/or amide group, polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, difunctional monomers having the formula:

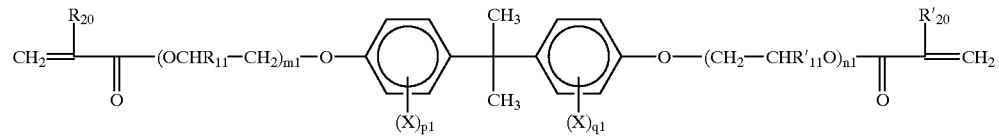

in which:
$R_{20}$, $R'_{20}$, $R_{11}$, and $R'_{11}$ are identical or different and represent, independently, a hydrogen or a methyl group;
$m_1$ and $n_1$ are, independently, integers between 0 and 4, inclusive;
X and X', which are identical or different, represent a halogen; and
$p_1$ and $q_1$ are, independently, integers between 0 and 4, inclusive, and copolymers of at least two types of copolymerisable monomers selected from the precursor monomers of the polymers listed above.

18. A cross-linked or non-cross-linked (co)polymer, characterised in that it comprises, as (co)monomer(s), at least one of the photochromic products according to claim 7.

19. A method for imparting a photochromic response to a material comprising:

disposing a compound according to claim 1 into or onto the material.

20. A method for imparting a photochromic response to a material comprising:

disposing a compound prepared by a method according to claim 4 into or onto the material.

21. An ophthalmic and/or solar article, charaeterised in that it comprises:

at least one photochromic product according to claim 5.

22. An article according to claim 21, characterised in that said article is a lens, a glazing, or an optical device.

23. An ophthalmic and/or solar article, characterised in that it comprises:

at least one photochromic product according to claim 7.

24. An article according to claim 23, characterised in that said article is a lens, a glazing, or an optical device.

25. An ophthalmic and/or solar article, characterised in that it comprises:

at least one photochromic composition according to claim 9.

26. An article according to claim 25, characterised in that said article is a lens, a glazing, or an optical device.

27. An ophthalmic and/or solar article, characterised in that it comprises:

at least one photochromic composition according to claim 14.

28. An article according to claim 27, characterised in that said article is a lens, a glazing, or an optical device.

29. An ophthalmic and/or solar article, characterised in that it comprises:

at least one cross-linked or non-cross-linked (co)polymer according to claim 13.

30. The article according to claim 29, characterised in that said article is a lens, a glazing, or an optical device.

31. An ophthalmic and/or solar article, characterised in that it comprises:

at least one cross-linked or non-cross-linked (co)polymer according to claim 18.

32. The article according to claim 31, characterised in that said article is a lens, a glazing, or an optical device.

* * * * *